(12) United States Patent
Merz et al.

(10) Patent No.: US 9,395,318 B2
(45) Date of Patent: *Jul. 19, 2016

(54) ELECTROCHEMICAL SENSOR DEVICE

(71) Applicant: ams International AG, Rapperswil-Jona (CH)

(72) Inventors: Matthias Merz, Leuven (BE); Dimitri Soccol, Rotselaar (BE)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 191 days.

This patent is subject to a terminal disclaimer.

(21) Appl. No.: 14/159,036

(22) Filed: Feb. 7, 2014

(65) Prior Publication Data

US 2014/0202855 A1 Jul. 24, 2014

(51) Int. Cl.
*G01N 27/26* (2006.01)
*G01N 27/404* (2006.01)
*G01N 33/00* (2006.01)

(52) U.S. Cl.
CPC ............ *G01N 27/26* (2013.01); *G01N 27/4045* (2013.01); *G01N 33/004* (2013.01)

(58) Field of Classification Search
CPC ................ G01N 27/404–27/407; G01N 33/00
See application file for complete search history.

(56) References Cited

U.S. PATENT DOCUMENTS

| | | | |
|---|---|---|---|
| 3,616,416 A | 10/1971 | Linenberg et al. | |
| 4,913,792 A * | 4/1990 | Nagata | G01N 27/4045 204/412 |
| 5,215,643 A * | 6/1993 | Kusanagi | G01N 27/4045 204/412 |
| 5,830,337 A | 11/1998 | Xu | |
| 6,376,124 B1 | 4/2002 | Dodgson et al. | |
| 8,852,513 B1 * | 10/2014 | Speer | G01N 33/0014 204/424 |
| 2003/0121781 A1 | 7/2003 | Prohaska et al. | |
| 2004/0026246 A1 | 2/2004 | Chapples et al. | |
| 2004/0026268 A1 | 2/2004 | Maki et al. | |
| 2008/0128285 A1* | 6/2008 | Moon | G01N 27/4045 205/80 |
| 2010/0133120 A1 | 6/2010 | Varney et al. | |
| 2011/0226619 A1 | 9/2011 | Eckhardt et al. | |
| 2011/0253534 A1 | 10/2011 | Eckhardt et al. | |
| 2012/0036921 A1 | 2/2012 | De Coulon et al. | |

(Continued)

FOREIGN PATENT DOCUMENTS

DE 10323858 A1 12/2004
EP 0125807 A2 11/1984

(Continued)

OTHER PUBLICATIONS

Gardner et al. (IEEE Sensors Journal, vol. 10, No. 12, Dec. 2010).*

(Continued)

*Primary Examiner* — Jennifer Dieterle
(74) *Attorney, Agent, or Firm* — McDermott Will & Emery LLP

(57) ABSTRACT

There is disclosed an electrochemical sensor device comprising: an integrated electrochemical sensor element having: a substrate; first and second electrodes formed on the upper surface of the substrate; and an electrolyte layer formed on the first and second electrodes so as to electrically contact both the first and second electrodes; and a sensor integrated circuit electrically connected to the first and second electrodes of the integrated electrochemical sensor element. The integrated electrochemical sensor element and the sensor integrated circuit are provided in a single package.

16 Claims, 9 Drawing Sheets

(56) References Cited

U.S. PATENT DOCUMENTS

| | | |
|---|---|---|
| 2012/0098075 A1 | 4/2012 | Lamagna et al. |
| 2013/0091924 A1 | 4/2013 | Scheffler et al. |
| 2013/0144131 A1 | 6/2013 | Wang et al. |

FOREIGN PATENT DOCUMENTS

| | | |
|---|---|---|
| EP | 0432757 A2 | 6/1991 |
| EP | 0514873 A1 | 11/1992 |
| EP | 0625704 A2 | 11/1994 |

OTHER PUBLICATIONS

Currie, J. F., et al, Micromachined Thin Film Solid State Electrochemical CO2, NO2, and SO2 Gase Sensors, Sensors and Actuators B 59, pp. 235-241 (1999).

Tan, Zhichao, et al., "A 1.8V 11 W CMOS Smart Humidity Sensor for RFID Sensing Application" IEEE Asian Solid State Circuits Conference, Nov. 14-16, 2011, Jeju, Korea, pp. 105-108 (Nov. 2011).

Wollenstein, J., et al, "A Novel Single Chip Thin Film Metal Oxide Array", Sensors and Actuators B 93, pp. 350-355 (2003).

Drager, "DragerSensor XXS CO", Multilingual Product Specification, 2 pages (2005).

Microsens, "Microsens Amperometric Sensor-Sensor Description", retrievied from internet Oct. 29, 2013 http://www.microsens.ch/products/pdf/Amperometric_Sensor.pdf, 2 pages.

Extended European Search Report for Application No. 13152411.8, dated Apr. 17, 2013, 10 pages.

Alphasense Limited; "Alphasense Application Note AAN 105-3 Designing a Potentiostatic Circuit"; Great Notley, Essex, UK; 5 pages (Mar. 2009).

Boutet et al., "Low power CMOS potentiostat for three electrodes amperometric chemical sensor", Faible Tension Faible Consommation (FTFC), 2011, IEEE, pp. 15-18, May 30, 2011.

DropSens; "Customised SPEs"; retreived from the internet Feb. 25, 2014 http://www.dropsens.com/en/pdfs_Productos/new_brochures/customised_Spes.pdf; 1 page.

Dubbe, A. "Fundamentals of solid state ionic micro gas sensors", Sensors and Actuators, vol. 88, No. 2, pp. 138-148, Jan. 15, 2003.

Yamazaki et al., "Design and Fabrication of Complementary Metal-Oxide-Semiconductor Sensor Chip for Electrochemical Measurement", Japaense Journal of applied Physics, vol. 49, No. 4, p. 04DL11, Apr. 1, 2010.

Wollenstein et al., "Material Properties and the influence of metallic catalysts at the surface of highly dense $SnO_2$ films" Sensors and Actuators B, vol. 70 (2000), pp. 196-202.

Wollenstein et al., "Preparation, morphology and gas-sensing behavior of $Cr_2$—$xTi_xO_{3+z}$ thin-films on standard silicon wafers" IEEE Sens. J., vol. 2 (2002), pp. 403-408.

UL 2034 "Standard for Single and Multiple Station Carbon Monoxide Alarms" UL LLC, issued Feb. 28, 2008.

DIN EN 50291-1 (VDE 0400-34-1); First Pages; 14 pages w/translation) (Nov. 2009).

UL, "Carbon Monoxide Alarm Considerations for Code Authorities", The Code Authority newsletter, Issue 3, 2009.

\* cited by examiner though in the detection of components in a gaseous medium.

Electrochemical sensors are well known in the art for use in the detection of components in a gaseous medium. The sensors generally comprise at least two electrodes, a working electrode and a counter electrode. The change in electrical impedance between the electrodes is determined, for example by applying a voltage of known value and form across the electrodes, as a result of the sensor being brought into contact with the gaseous medium. In many cases, the electrodes are coated with an electrolytic or semiconductor material that bridges the electrodes, the apparent conductivity of which changes as a result of contact with the gaseous medium.

Electrochemical gas sensors are used in a wide variety of applications e.g. for safety (detection of toxic gas concentrations) or environmental monitoring.

Conventional electrochemical sensors are, however, typically large in size and expensive. This is primarily due to the separate electrochemical cell and read-out electronics which need to be connected by a Printed Circuit Board (PCB). Furthermore, in order to achieve sufficient sensor accuracy, the electrochemical sensor element should be large enough to generate sufficient current for measurement by the (typically distant) read-out electronics. This also contributes to the size of conventional electrochemical sensors.

According to an aspect of the invention, there is provided an electrochemical sensor device according to claim 1.

Embodiments may further comprise a filter to increase the selectivity of the electrochemical sensor element.

A reference electrode may be formed on the upper surface of the substrate below the electrolyte layer.

The thickness of the electrolyte layer may be 10 μm or less, and the area of the first and second electrodes electrically contacting the electrolyte layer may be in the range of 0.01 mm$^2$ to 11 mm$^2$.

Embodiments may provide a packaged electrochemical sensor device having an integrated electrochemical sensor element and sensor integrated circuit formed on a single die. In other embodiments, the integrated electrochemical sensor element and the sensor integrated circuit may be formed on separate dies but provided in a single package (e.g. packaged in the same discrete component).

Thus, embodiments may provide a packaged gas sensor device that comprises an electrochemical sensor element and an electrical read-out circuit integrated within the single package. Co-integration of the sensor element and read-out electronics in the same discrete package may enable considerable reduction in overall system size and cost.

The electrochemical sensor and electrical read-out circuit may be further integrated on top of a conventional CMOS chip or die.

In other words, embodiments may provide for the integration of an electrochemical sensor element together with the read-out electronics in a single discrete package. This may be done using two separate dies (one for the electrochemical sensor element and the other for a read-out integrated circuit (IC)) and electrically connecting the separate dies by bond wires. Alternatively, the electrochemical sensor element may be manufactured on the same die as the read-out IC to provide an even smaller form factor whilst using CMOS processes. Here, additional processing steps may only be needed after undertaking conventional processing, thus avoiding changes to existing processes.

Additional sensor elements adapted to sense of parameters such as temperature, relative humidity, ambient light etc. may also be included in the same package. Such further sensors may be used to provide additional environmental information, and may also be used to correct for altered sensitivity of the electrochemical sensor element (due to temperature or relative humidity for example) thereby improving the accuracy of an electrochemical sensor device according to an embodiment.

Examples of the invention will now be described in detail with reference to the accompanying drawings, in which.

The terms, chip, integrated circuit, monolithic device, semiconductor device, and microelectronic device, are often used interchangeably in this field. The present invention is applicable to all the above as they are generally understood in the field.

The terms metal line, interconnect line, trace, wire, conductor, signal path and signalling medium are all related. The related terms listed above, are generally interchangeable, and appear in order from specific to general. In this field, metal lines are sometimes referred to as traces, wires, lines, interconnect or simply metal. Metal lines, generally aluminum (Al), copper (Cu) or an alloy of Al and Cu, are conductors that provide signal paths for coupling or interconnecting, electrical circuitry. Conductors other than metal are available in microelectronic devices. Materials such as doped polysilicon, doped single-crystal silicon (often referred to simply as diffusion, regardless of whether such doping is achieved by thermal diffusion or ion implantation), titanium (Ti), molybdenum (Mo), and refractory metals are examples of other conductors.

The terms contact and via, both refer to structures for electrical connection of conductors at different interconnect levels. These terms are sometimes used in the art to describe both an opening in an insulator in which the structure will be completed, and the completed structure itself. For purposes of this disclosure contact and via refer to the completed structure.

The term vertical, as used herein, means substantially orthogonal to the surface of a substrate. Also, terms describing positioning or location (such as above, below, top, bottom, etc) are to be construed in conjunction with the orientation of the structures illustrated in the diagrams.

There is proposed an integrated electrochemical sensor element that may be manufactured using IC processing techniques, thereby enabling a significant reduction in size when compared to conventional electrochemical sensors.

To assess possible scaling of an electrochemical sensor element (or cell), the relation between electric current and gas concentration in air will now be analysed. In essence, the measured current is a combination of three processes. In the following section, a short analysis is included, resulting in a formula to estimate the maximum obtainable current for a given electrode surface area, gas concentration and electrolyte thickness.

Figure 1:
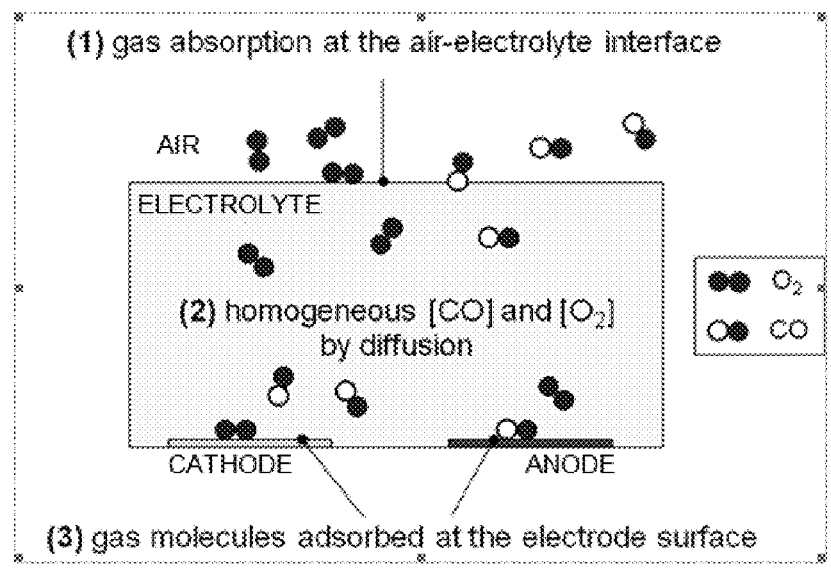
FIG. 1 illustrates an initial equilibrium situation within an electrochemical sensor element for the electrochemically active gases involved in carbon monoxide sensing.

The initial equilibrium situation within an electrochemical sensor element is illustrated in FIG. 1 for the electrochemically active gases involved in carbon monoxide (CO) sensing. More specifically, the concentration of CO and $O_2$ gas molecules in the electrolyte is in equilibrium with the gas partial pressure. In the pressure range of interest, this equilibrium concentration is directly proportional to the gas concentration. This is described by Henry's law (here shown for CO) in the following equation (Equation 1):

$$p_{CO} = k_H x_{CO} \quad (1),$$

where $p_{CO}$ is the CO partial pressure, $k_H$ the Henry constant and $x_{CO}$ the mole fraction of CO in the solvent. The mole fraction can easily be recalculated into the concentration of CO using the following equation (Equation 2):

$$c_{CO} = \frac{x_{CO}}{1 - x_{CO}} c_{solvent}. \quad (2)$$

This concentration will always exist at the air-electrolyte interface (see label "(1)" in FIG. 1). In the absence of electrochemical processes (e.g. at open circuit potential), the concentration will be uniform throughout the electrolyte and at the electrode surfaces by diffusion of the gas molecules (see label "(2)" in FIG. 1). The gas molecules are the electrochemically active species in this system. When adsorbed at the electrode surface, they give rise to a mixed electrode potential which is determined by the Nernst law as described in the following equation (Equation 3):

$$E_{mix} = \frac{E_0^{CO} + E_0^{O_2}}{2} - \frac{59.6 \text{ mV}}{n} \log \frac{[CO]}{[O_2]^{1/2}}, \quad (3)$$

wherein $E_0^{CO}$ and $E_0^{O_2}$ are the standard electrode potentials for CO and $O_2$ (−0.11 and +0.4 V vs. SHE), respectively, and n is the number of electrons involved in the electrochemical reaction (here, n=2).

Figures 2A, 2B, 2C:
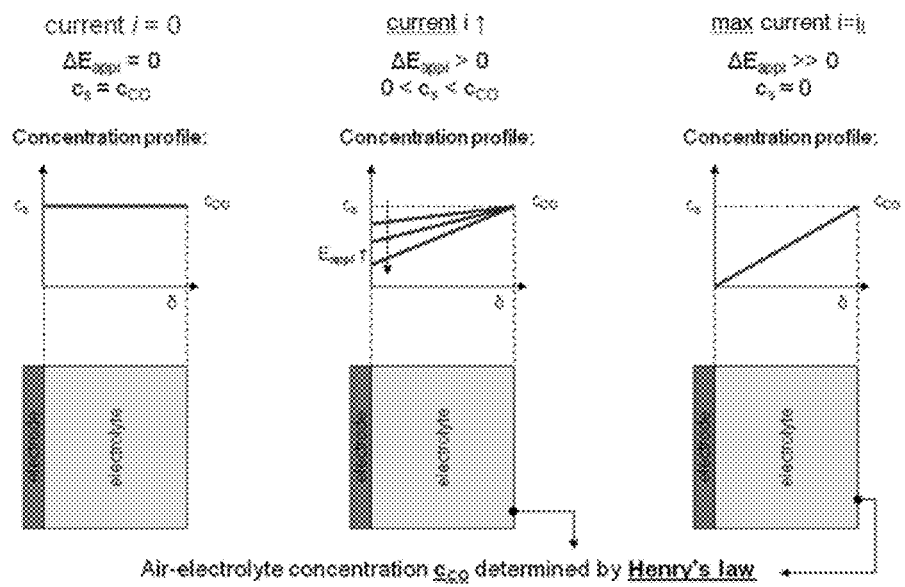
FIGS. 2A-2C illustrate the various concentration profile for various values of externally applied potential difference.

Without any externally applied potential difference, the mixed electrode potential exists at both the sensing and counter electrode. This situation is represented by FIG. 2A.

Once a potential difference is applied between the sensing and counter electrodes, a new surface equilibrium concentration sets in (as described by the Nernst law). At the positively polarized electrode (i.e. the anode or sensing electrode), the CO molecules are oxidized into $CO_2$, while $O_2$ is reduced to $OH^−$ at the cathode (i.e. counter electrode). Up to moderate potential differences, it is the applied potential difference that determines the measured current. This regime, called the reaction limited regime, is represented by FIG. 2B. Because the measured current not only depends on the gas concentration in air but also on the applied potential, this regime is less suited for gas sensing.

Further increase of the potential difference decreases the surface concentration of gas molecules such that it comes close to zero. From this point onward, the reaction rate (the measured current) does not increase any more with an increasing potential difference. Instead, the current is limited by diffusion of CO molecules towards the electrodes. The resulting limiting current is the maximum current that can be obtained. This regime is represented in FIG. 2C.

Figure 3:
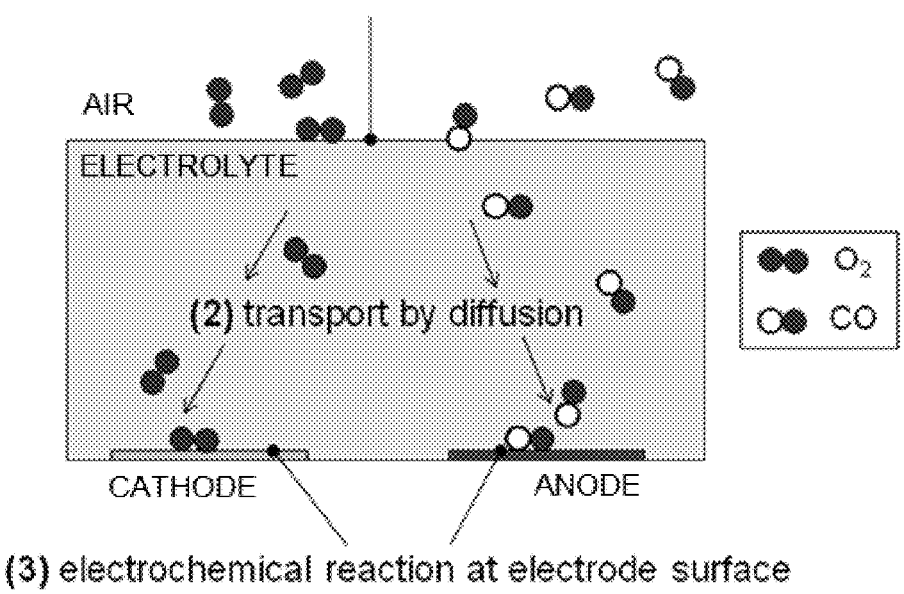
FIG. 3 illustrates a full current situation within an electrochemical sensor element for the electrochemically active gases involved in carbon monoxide sensing.

The full current is now determined by the process of gas absorption (according to Henry's law) and diffusion towards the electrode, where CO is immediately oxidized. This limiting case is shown in more detail in FIG. 3.

The limiting current $i_l$ in this regime can be calculated by the following equation (Equation 3):

$$i_l = \frac{nFAD_{CO}c_{CO}}{\delta}, \quad (3)$$

wherein n is the number of electrons involved in the reaction, F is Faraday's constant, A is the electrode surface area, $D_{CO}$ is the diffusion constant of CO in the electrolyte, $C_{CO}$ the concentration of CO molecules at the air-electrolyte interface (determined by Henry's law), and $\delta$ the thickness of the electrolyte. Combining Henry's law (Equation 1 and Equation 2) with the formula for the diffusion limiting current (Equation 3) gives the following equation (Equation 4) that allows for estimating the maximum current as a function of gas pressure:

$$i_l = \frac{nFAD_{CO}}{\delta} \frac{p_{CO}}{k_H - p_{CO}} c_{solvent}. \quad (4)$$

In Table 1 below, the material constants $D_{CO}$, $k_H$ and $C_{solvent}$ are detailed for two exemplary electrolytes, namely water ($H_2O$) and an ionic liquid [Bmim][NTf$_2$]. The data clearly shows that the mobility of CO molecules is higher in aqueous environments compared to the ionic liquid. However, the solubility of CO in the ionic liquid is higher.

| | $D_{CO}$ [m$^2$/s] | $k_H$ (CO) atm | $c_{solvent}$ [mole/m$^3$] | A [mm$^2$] |
|---|---|---|---|---|
| $H_2O$ | 10e−10 | 58280 | 55.5e3 | 0.16 |
| [Bmim][NTf$_2$] | 0.4e−10 | 950 | 3.4e3 | 1.1 |

Using CMOS technology, it may be possible to resolve currents of about 15 pA. Assuming a minimal required resolution of 5 ppm CO and using the parameters for the example electrolytes above, the minimal form factor A(electrode)/$\delta$ (electrolyte) can be calculated. Thus, the minimal electrode surface area for a 10 μm thick electrolyte is also shown in Table 1. It has therefore been identified that a minimal electrode surface area of 0.16 mm$^2$ to 1.1 mm$^2$ may be required to detect 5 ppm CO for a 10 μm thick electrolyte. For these electrolytes, further downscaling can be achieved by decreasing the electrolyte thickness or increasing the resolution and accuracy of the current measurement circuit Referring to FIG. 4, there is illustrated a packaged electrochemical sensor device 10 according to an embodiment of the invention. The electrochemical sensor device 10 comprises an integrated electrochemical sensor element 12 according to an embodiment of the invention and a sensor integrated circuit (IC) (or CMOS chip) 14 electrically connected to the integrated electrochemical sensor element 12.

The integrated electrochemical sensor element comprises first 16 and second 18 electrodes formed on the upper surface of a substrate 20, and an electrolyte 19 formed on the first 16 and second 18 electrodes so as to electrically contact both the first 16 and second 18 electrodes. The first 16 and second 18 electrodes are each electrically connected to the sensor IC 14 via respective bond wires 22A and 22B. Here, it is also noted that the first 16 and second 18 electrodes are formed from Platinum (Pt), although it will be understood that other suitable materials made be used for the electrodes, such as Au and Pd for example (in addition Ag or AgCl may be used as material for reference electrodes).

The sensor IC 14 is connected to first 24 to third 26 input/output terminals of the packaged electrochemical sensor device 10 to provide for the input and/or output of signals to the sensor IC 14.

Here, the integrated electrochemical sensor element 12 and sensor IC 14 are provided on separate dies within the packaging of the device 10. In alternative embodiment, the integrated electrochemical sensor element 12 and sensor IC 14 may be formed on the same die.

Figure 4:
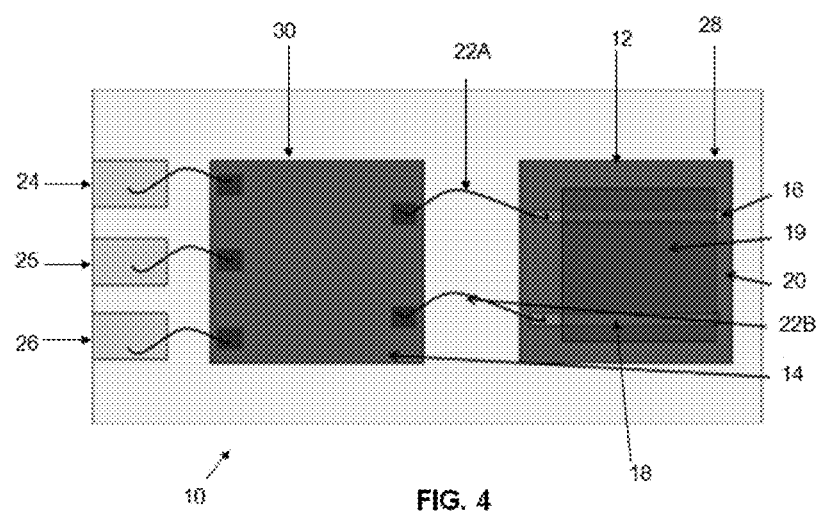
FIG. 4 illustrates an electrochemical sensor device according to an embodiment of the invention.
Figure 5:
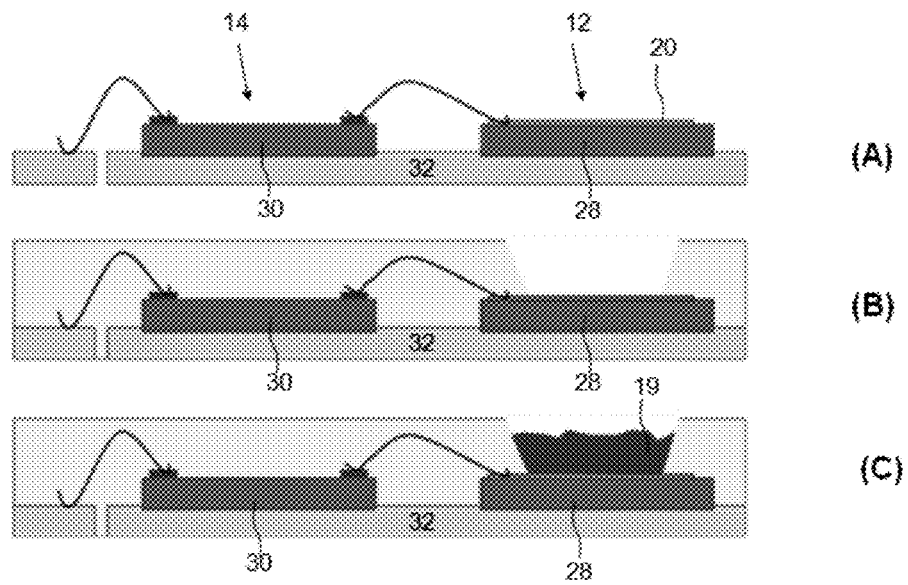
FIGS. 5A-5C show the steps of manufacturing the device of FIG. 4.

Referring now to FIG. 5, there is illustrated a method of manufacturing the device of FIG. 4, wherein the integrated electrochemical sensor element 12 and sensor IC 14 are provided on separate dies within the packaging of the device 10. Firstly, the first 16 and second 18 electrodes of the electrochemical sensor element 12 are patterned on a glass substrate 20. provide on a first die 28, and a CMOS wafer (containing a plurality of sensor ICs) is diced into individual dies 30 each having a sensor IC 14 provided thereon. Thus, a second die 30 having a sensor IC 14 thereon is obtained.

The first 28 and second 30 dies are attached to a lead frame/support 32, and the first 16 and second 18 electrodes are electrically connected to the sensor IC on the second die 30 via wire bonds 22 to provide the structure shown in FIG. 5A.

Subsequent overmolding and curing (i.e. encapsulation) is illustrated in FIG. 5B. Here open cavity molding leaves a cavity directly on top of the first die 28).

An electrolyte 19 is then applied to electrochemical sensor element 12, for example by an inkjet or micro drop process to provide the structure shown in FIG. 5C. The deposited electrolyte 19 contacts the first 16 and second 18 electrodes of the electrochemical sensor elements 12

Figure 6:
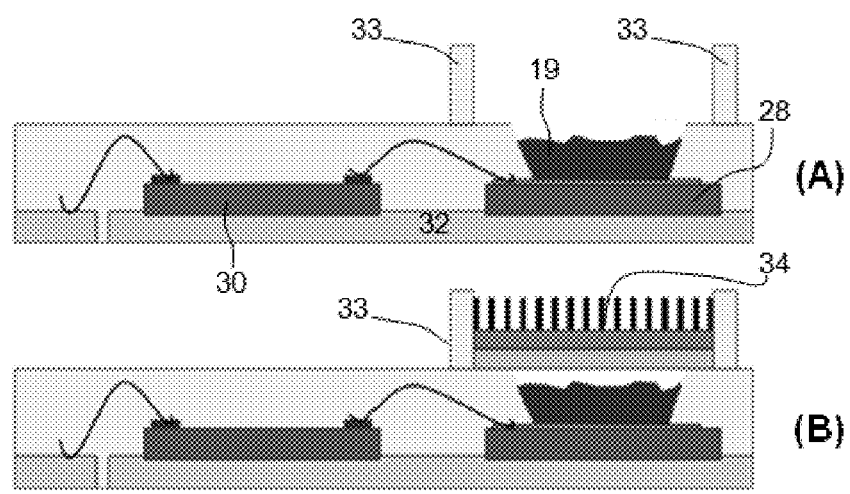
FIGS. 6A-6B show a modification to the embodiment of FIG. 4.

Turning now to FIG. 6, a modification to the embodiment of FIG. 4 is shown. More specifically, the method of embodiment of FIG. 4 is modified to include a filter positioned directly above the electrolyte 19.

Here, the structure shown in FIG. 5C is modified by the addition of suitable structures 33 (e.g. rings) for attachment during overmolding (by adaptation of the molding form). The addition of such structures is shown in FIG. 6A.

Individual filter layers 34 can be cut with a punch tool and applied (by a pick and place machine) above the electrolyte 19 (and within area defined by the structures 33). Moreover, a rigid yet transparent to gas material (e.g. polymer mesh or plate with holes) can be applied as the top layer for mechanical protection Referring now to FIG. 7, there is illustrated a method of manufacturing a device according to an alternative embodiment, wherein the integrated electrochemical sensor element and sensor IC are provided on a single die.

Firstly, there is provided a die 70 with integrated sensor IC and bond pads 14 as shown in FIG. 7A. The bond pads 14 are provided to cater for bond wire connections to be made to the integrated sensor IC (see FIG. 7C)

Next, Pt electrodes are deposited on a substrate 72 and patterned using known techniques. The resultant structure is the attached to the die 70 to provide the die structure shown in FIG. 7B, wherein the Pt electrodes are electrically connected to the sensor IC 14 via Tungsten vias (not shown). Alternatively the Pt electrodes may be deposited and patterned directly on top of the die 70 (with electrodes connected to the underlying circuit by vias), so no extra substrate and die attach/stacking is needed.

This is then attached to a lead frame/support 74, and the sensor IC is electrically connected to the lead frame/support contacts via wire bonds 76 to provide the structure shown in FIG. 7C.

Subsequent encapsulation e.g. by open cavity molding (overmolding) and curing is illustrated in FIG. 7D, wherein the Pt electrodes on the substrate 72 are at least partially exposed. For example, the sensor IC and the integrated electrochemical sensor element are at least partially encapsulated in resin, wherein a cavity is formed in the resin which exposes the electrodes of the integrated electrochemical sensor element.

An electrolyte 19 is then applied to cover the exposed Pt electrodes, for example by an inkjet or micro drop process to provide the structure shown in FIG. 7E. The deposited electrolyte 19 therefore contacts the electrode of the electrochemical sensor element.

Figure 7:
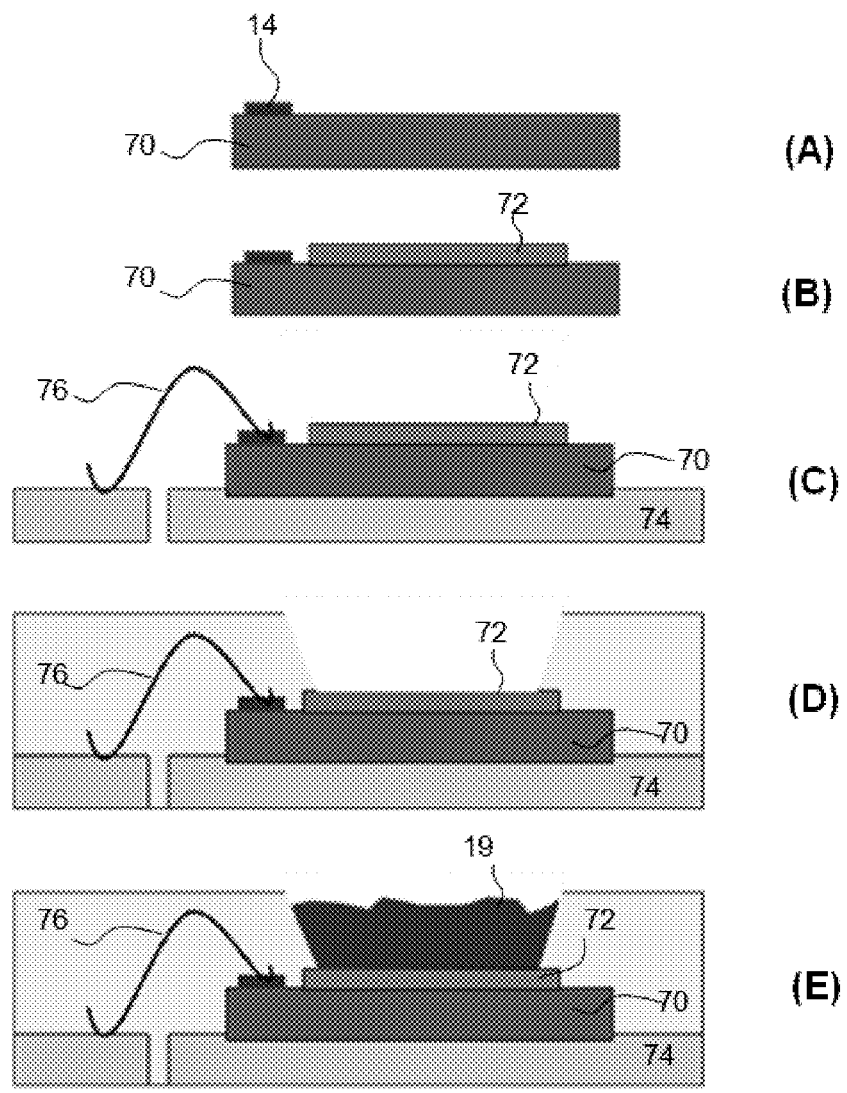
FIGS. 7A-7E illustrate the steps of manufacturing a device according to an alternative embodiment.

As with the embodiment comprising separate dies for the sensor IC and the electrochemical sensor element, the embodiment of FIG. 7 may be modified to further comprise one or more filters positioned directly above the electrolyte 19.

Further, in alternative embodiments, a plurality of integrated electrochemical sensor elements may be provided within a single discrete package (either on the same die or on separate dies).

It will be understood that the actual electrolyte volume in an electrochemical sensor element according to an embodiment may be very small. In order to prevent evaporation, ionic liquids (which have low vapour pressure, and thus reduced evaporation ability) or solid electrolytes may be used as an electrolyte in an embodiment. Alternatively, one of the filter layers may be chosen so at to restrict or prevent electrolyte evaporation.

The embodiments described above have been detailed as having first and second electrodes (i.e. the working and counter electrodes). An electrochemical sensor element according to an embodiment of the invention may also comprise a third electrode (commonly referred to as a reference electrode) in contact with the electrolyte. In some embodiments, the working and counter electrodes may be made from Platinum (Pt) while the reference electrode may be made from Ag/AgCl. It will be understood, however, that other metals may be used depending on the chemical reactions involved.

Figure 8:
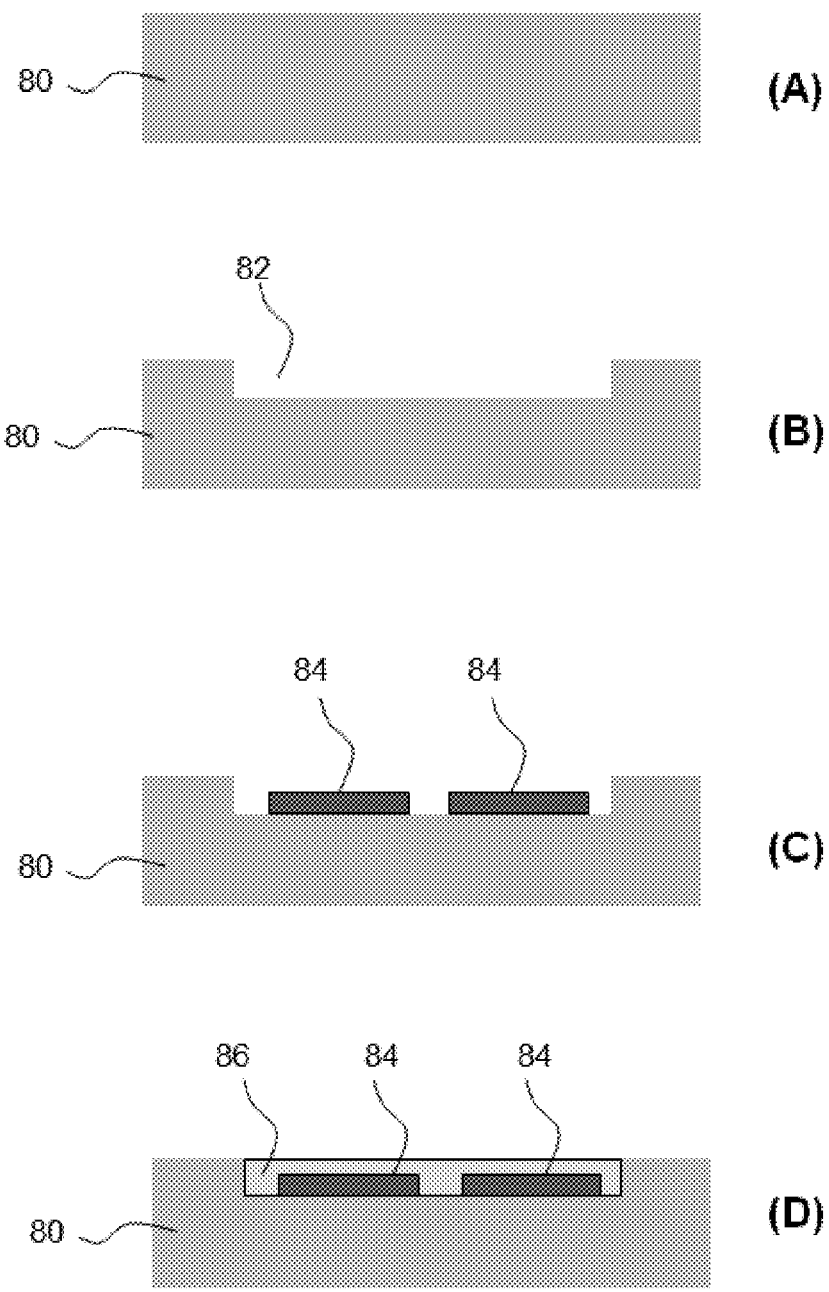
FIGS. 8A-8D illustrate a method of manufacturing an integrated electrochemical sensor element for a device according to an embodiment.

Referring now to FIG. 8, there is illustrated a method of manufacturing an integrated electrochemical sensor element for a device according to an alternative embodiment.

Firstly, there is provided a substrate 80 as shown in FIG. 8A. The substrate 80 is then etched so as to form a cavity 82 in the upper surface of the substrate 80 as shown in FIG. 8B.

Next, Pt electrodes 84 are deposited on the substrate 82 within the cavity 82 and patterned using known techniques.

The resultant structure is shown in FIG. 7C, wherein the Pt electrodes 84 are situated in the cavity 84 of the substrate 84.

An electrolyte 86 is then deposited to fill the cavity 82 and cover the electrodes 84 as shown in FIG. 7D. The deposited electrolyte 86 therefore covers and contacts the electrodes 84 of the electrochemical sensor element.

This approach avoids the deposition of electrolyte on individually packaged sensor devices. Instead, the cavities, electrodes and electrolyte of electrochemical sensor elements according to embodiments may be processed on a wafer-scale, thereby helping to decrease the cost of manufacturing.

Figure 9:
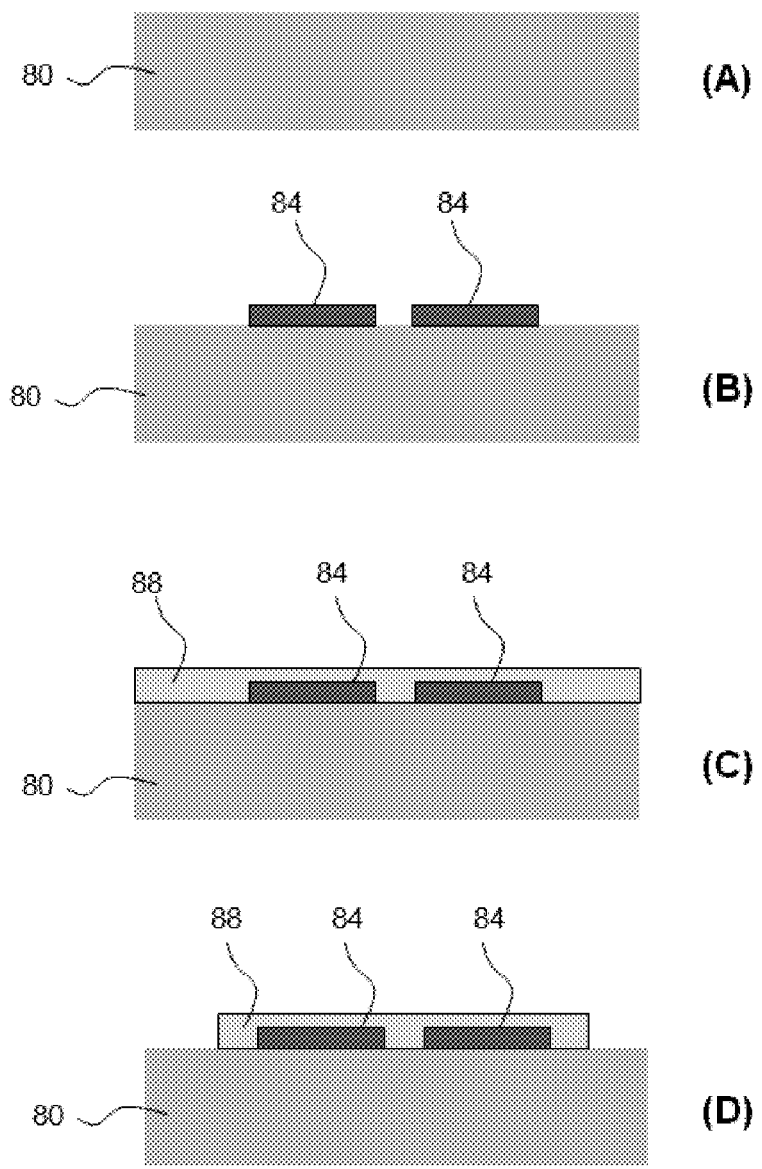
FIGS. 9A-9D illustrate a method of manufacturing an integrated electrochemical sensor element for a device according to an alternative embodiment.

A modification to the method of FIG. 8 is illustrated in FIG. 9, wherein a cavity is not formed in the substrate but, instead, a solid electrolyte is deposited over the electrode and patterned by photo-litho. Firstly, there is provided a substrate 80 as shown in FIG. 9A. Next, Pt electrodes 84 are deposited on the upper surface of the substrate 80 and patterned using known techniques to provide the structure shown in FIG. 9B. A solid electrolyte 88 is then deposited to cover the upper surface of the substrate 80 and the electrodes 84 as shown in FIG. 9C. The deposited electrolyte 88 therefore covers and contacts the electrodes 84 of the electrochemical sensor element. Finally, the electrolyte 88 is patterned by photo-lithography so to remove one or more portions of the electrolyte 88 and provide the final structure as shown in FIG. 9D.

As for the embodiment of FIG. 8, the modified method shown in FIG. 9 enables processing at the wafer level. Accordingly, an electrochemical sensor element manufactured according to such a method may be cheap (due to mass-production. Further, this type of processing is possible "on-top of" CMOS or can be fabricated on a separate die and subsequently be packaged together with the read-out electronics (e.g. sensor IC).

Also, it is noted that although an embodiment described above (in conjunction with FIG. 5) has been detailed as employing a glass substrate, alternative embodiments may employ any other suitable insulating substrate, such as a Si substrate for example. A Si substrate, however, is semiconducting which may cause direct currents between electrodes through substrate. Thus, for such embodiments, it may be preferable to also employ a dielectric insulation layer (e.g. $SiO_2$ or SiN) on top of the Si substrate prevent such currents. The electrodes can then be patterned on top of the insulation layer.

It is also noted that planar electrode arrangements may be suitable, since this can be easily achieved with conventional semiconductor technologies. Also, to increase the overall area of the electrodes, the electrode may be formed in special shapes, such a meanders, rings, etc.

Various modifications will be apparent to those skilled in the art.

The invention claimed is:

1. An electrochemical sensor device comprising:
    an integrated electrochemical sensor element having: a substrate; first and second electrodes formed on the upper surface of the substrate; and an electrolyte layer formed on the first and second electrodes so as to electrically contact both the first and second electrodes;
    a sensor integrated circuit electrically connected to the first and second electrodes of the integrated electrochemical sensor element, wherein the integrated electrochemical sensor element and the sensor integrated circuit are provided in a single package; and
    an overmold having a cavity situated above the integrated electrochemical sensor element, wherein the electrolyte layer is formed in the cavity.

2. The electrochemical sensor device of claim 1, wherein the integrated electrochemical sensor element further comprises:
    a filter layer formed above the electrolyte layer, the filter layer being adapted to block one or more components of a gaseous medium.

3. The electrochemical sensor device of claim 1, wherein the integrated electrochemical sensor element further comprises:
    a reference electrode formed on the upper surface of the substrate below the electrolyte layer, the electrolyte layer electrically contacting the reference electrode,
    and wherein the reference electrode is electrically connected to the integrated circuit.

4. The electrochemical sensor device of claim 1, wherein the thickness of the electrolyte layer is 10 μm or less,
    and wherein the area of the first and second electrodes electrically contacting the electrolyte layer is 11 $mm^2$ or less.

5. The electrochemical sensor device of claim 1, wherein the upper surface of the substrate comprises a cavity within which the first and second electrodes are formed, and wherein the electrolyte layer is formed in the cavity so as to fill the cavity and cover the first and second electrodes.

6. The electrochemical sensor device of claim 1, wherein the integrated electrochemical sensor element and the sensor integrated circuit are formed on a single die.

7. The electrochemical sensor device of claim 6, wherein the sensor integrated circuit is electrically connected the first and second electrodes of the integrated electrochemical sensor element via one or more vias.

8. The electrochemical sensor device of claim 1, wherein the integrated electrochemical sensor element and the sensor integrated circuit are formed on separate dies, and wherein the sensor integrated circuit is electrically connected the first and second electrodes of the integrated electrochemical sensor element via one or more bond wires.

9. The electrochemical sensor device of claim 1 further comprising an additional sensing element adapted to determine temperature.

10. A method of manufacturing a packaged electrochemical sensor device comprising the steps of:
    forming an integrated electrochemical sensor element having: first and second electrodes on the upper surface of a substrate; and an electrolyte layer electrically contacting both the first and second electrodes;
    electrically connecting the first and second electrodes to a sensor integrated circuit; and
    placing the sensor integrated circuit and the integrated electrochemical sensor element in a single package;
    providing for an overmold having a cavity situated above the integrated electrochemical sensor element, wherein the electrolyte layer is formed in the cavity.

11. The method of claim 10, further comprising the step of forming a filter layer above the electrolyte layer, the filter layer being adapted to block one or more components of a gaseous medium.

12. The method of claim 10, further comprising:
    forming a reference electrode on the upper surface of the substrate below the electrolyte layer, the electrolyte layer electrically contacting the reference, and
    electrically connecting the reference electrode to the sensor integrated circuit.

13. The method of claim 10, comprising forming the integrated electrochemical sensor element and the sensor integrated circuit on a single die.

14. The method of claim 10, comprising forming the integrated electrochemical sensor element and the sensor integrated circuit on separate dies,
and wherein electrically connecting the sensor integrated circuit to the first and second electrodes of the integrated electrochemical sensor element comprises electrically connecting the sensor integrated circuit to the first and second electrodes of the integrated electrochemical sensor element via one or more bond wires.

15. An electrochemical sensor device comprising:
an integrated electrochemical sensor element having: a substrate; first and second electrodes formed on the upper surface of the substrate; and an electrolyte layer formed on the first and second electrodes so as to electrically contact both the first and second electrodes; and
a sensor integrated circuit electrically connected to the first and second electrodes of the integrated electrochemical sensor element,
wherein the integrated electrochemical sensor element and the sensor integrated circuit are provided in a single package,
wherein the upper surface of the substrate comprises a cavity within which the first and second electrodes are formed,
wherein the electrolyte layer is formed in the cavity so as to fill the cavity and cover the first and second electrodes,
wherein the integrated electrochemical sensor element and the sensor integrated circuit are formed on a single die, and
wherein the substrate is a silicon substrate.

16. A method of manufacturing a packaged electrochemical sensor device comprising the steps of:
forming an integrated electrochemical sensor element having: first and second electrodes on the upper surface of a substrate; and an electrolyte layer electrically contacting both the first and second electrodes;
electrically connecting the first and second electrodes to a sensor integrated circuit;
placing the sensor integrated circuit and the integrated electrochemical sensor element in a single package; and
forming the integrated electrochemical sensor element and the sensor integrated circuit on a single die,
wherein the upper surface of the substrate comprises a cavity within which the first and second electrodes are formed,
wherein the electrolyte layer is formed in the cavity so as to fill the cavity and cover the first and second electrodes, and
wherein the substrate is a silicon substrate.

* * * * *